(12) United States Patent
Laugier et al.

(10) Patent No.: US 9,339,590 B2
(45) Date of Patent: *May 17, 2016

(54) BIOMATERIAL, INJECTABLE IMPLANT COMPRISING IT, ITS METHOD OF PREPARATION AND ITS USES

(75) Inventors: Elisabeth Laugier, Geneva (CH); Frank Gouchet, La Ferte Saint-Aubin (FR); Bernard Grandmontagne, Plouguerneau (FR)

(73) Assignee: Cutanea Life Sciences, Inc., Wayne, PA (US)

( * ) Notice: Subject to any disclaimer, the term of this patent is extended or adjusted under 35 U.S.C. 154(b) by 1368 days.

This patent is subject to a terminal disclaimer.

(21) Appl. No.: 11/677,389

(22) Filed: Feb. 21, 2007

(65) Prior Publication Data

US 2007/0202142 A1 Aug. 30, 2007

(30) Foreign Application Priority Data

Feb. 24, 2006 (FR) ...................................... 06 01657

(51) Int. Cl.
*A61F 2/10* (2006.01)
*A61K 9/14* (2006.01)
(Continued)

(52) U.S. Cl.
CPC ................ *A61L 27/52* (2013.01); *A61K 8/0241* (2013.01); *A61K 8/042* (2013.01); *A61K 8/736* (2013.01); *A61L 27/20* (2013.01); *A61L 27/50* (2013.01);
(Continued)

(58) Field of Classification Search
CPC ......... A61L 27/52; A61L 27/20; A61L 27/50; A61L 27/58; A61K 8/042; A61K 8/732; A61K 8/0241; A61K 2800/412; A61K 2800/91; A61Q 19/00; A61Q 19/08; A61Q 11/00; C08L 5/08

USPC .................. 424/422, 426, 428, 488, 70.13
See application file for complete search history.

(56) References Cited

U.S. PATENT DOCUMENTS 5,143,724 A * 9/1992 Leshchiner et al. ........ 424/78.08
5,258,028 A 11/1993 Ersek et al. ..................... 623/11
(Continued)

FOREIGN PATENT DOCUMENTS

| | | |
|---|---|---|
| EP | 0 251 695 | 1/1988 |
| EP | 0 648 480 | 4/1995 |

(Continued)

OTHER PUBLICATIONS

Syringe Needle Conversion Chart, Jun. 4, 2005, pp. 1-2.*
(Continued)

*Primary Examiner* — Brian-Yong Kwon
*Assistant Examiner* — Miriam A Levin
(74) *Attorney, Agent, or Firm* — Greenberg Traurig, LLP

(57) ABSTRACT

This invention relates to a biomaterial comprising an injectable bioresorbable polysaccharide composition wherein the polysaccharide may be succinochitosan glutamate. This invention also relates to a biomaterial comprising an injectable bioresorbable polysaccharide composition in which resorbable particles may be in suspension, the said particles comprising or consisting essentially of chitin and/or chitosan, which may be free of any additional formulation modifying agents, and a process for manufacturing the same. This invention also relates to a medical device including said biomaterial and to a method of repair or treatment including the filling of cavities in the human face or body.

8 Claims, 1 Drawing Sheet

(51) Int. Cl.

| | |
|---|---|
| *A61K 8/73* | (2006.01) |
| *C08B 37/08* | (2006.01) |
| *A61L 27/52* | (2006.01) |
| *C08L 5/08* | (2006.01) |
| *A61K 8/04* | (2006.01) |
| *A61L 27/20* | (2006.01) |
| *A61L 27/50* | (2006.01) |
| *A61Q 19/00* | (2006.01) |
| *A61Q 19/08* | (2006.01) |
| *A61Q 11/00* | (2006.01) |
| *A61L 27/58* | (2006.01) |
| *A61K 8/02* | (2006.01) |

(52) U.S. Cl.
CPC ............. *A61L 27/58* (2013.01); *A61Q 11/00* (2013.01); *A61Q 19/00* (2013.01); *A61Q 19/08* (2013.01); *C08L 5/08* (2013.01); *A61K 2800/412* (2013.01); *A61K 2800/91* (2013.01)

(56) References Cited

U.S. PATENT DOCUMENTS

| | | | | |
|---|---|---|---|---|
| 5,300,494 | A * | 4/1994 | Brode et al. | 514/55 |
| 5,451,406 | A | 9/1995 | Lawin et al. | 424/423 |
| 5,599,916 | A * | 2/1997 | Dutkiewicz et al. | 536/20 |
| 5,658,593 | A | 8/1997 | Orly et al. | 424/499 |
| 5,731,298 | A | 3/1998 | Reinmuller | 514/54 |
| 6,054,462 | A * | 4/2000 | Fran.cedilla.ois et al. | 514/275 |
| 6,130,321 | A * | 10/2000 | Johnson et al. | 536/20 |
| 6,387,978 | B2 * | 5/2002 | Ronan et al. | 523/113 |
| 6,413,526 | B1 | 7/2002 | Bazin et al. | |
| 6,716,251 | B1 | 4/2004 | Asius et al. | 623/23.58 |
| 7,098,194 | B2 | 8/2006 | Chenite et al. | |
| 7,776,840 | B2 * | 8/2010 | Bitterman | A61K 31/722 514/54 |
| 7,981,872 | B2 * | 7/2011 | Hardy | A61K 31/722 514/23 |
| 8,106,030 | B2 * | 1/2012 | Hardy | A61K 31/722 514/54 |
| 8,445,463 | B2 * | 5/2013 | Bitterman | A61K 31/722 514/55 |
| 8,445,464 | B2 * | 5/2013 | Bitterman | A61K 31/722 514/55 |
| 8,450,296 | B2 * | 5/2013 | Bitterman | A61K 31/722 514/55 |
| 9,029,350 | B2 * | 5/2015 | Bitterman | A61K 31/722 514/55 |
| 2003/0057159 | A1 * | 3/2003 | Struszczyk et al. | 210/702 |
| 2003/0091851 | A1 * | 5/2003 | Khor et al. | 428/532 |
| 2004/0092011 | A1 | 5/2004 | Wilkison et al. | |
| 2004/0191323 | A1 * | 9/2004 | Asius et al. | 424/489 |
| 2004/0228886 | A1 * | 11/2004 | Ding et al. | 424/401 |
| 2005/0106256 | A1 | 5/2005 | Hung et al. | 424/484 |
| 2005/0178396 | A1 | 8/2005 | Hunter et al. | |
| 2005/0208122 | A1 | 9/2005 | Allen et al. | 424/450 |
| 2006/0173551 | A1 | 8/2006 | Hubbard et al. | |
| 2006/0177480 | A1 | 8/2006 | Sung et al. | |
| 2007/0077305 | A1 | 4/2007 | Le et al. | 424/488 |
| 2008/0008738 | A1 | 1/2008 | Oliver et al. | 424/426 |

FOREIGN PATENT DOCUMENTS

| | | | |
|---|---|---|---|
| EP | 0 711 548 | 5/1996 | |
| FR | 2733426 | * 10/1996 | |
| FR | WO 9703708 A1 | * 2/1997 | ............. A61L 15/28 |
| JP | 10175857 A | * 6/1998 | ........... A61K 31/195 |
| WO | WO 96/33751 | 10/1996 | |
| WO | WO 01/87988 | * 11/2001 | |
| WO | WO 02/40072 | 5/2002 | |
| WO | WO 2004/020473 | 3/2004 | |
| WO | WO 2005/105058 | 11/2005 | |
| WO | WO 2006/048829 | * 5/2006 | |
| WO | WO 2007/096748 | 8/2007 | |
| WO | WO 2008/103594 | 8/2008 | |

OTHER PUBLICATIONS

Tanveer Ahmad Khan, Kok Khiang Peh and Hung Seng Ch'ng, Reporting degree of deacetylation values of chitosan: the influence of analytical methods, 2002, J Pharm Pharmaceut Sci 5(3), pp. 205-212.*
Bibliographic Data for ITRM20040539, p. 1.*
FR2733426 machine translation, publication date: Oct. 1996, pp. 1-3.*
Mi, Fwu-Long, et al., Biomaterials 23 (2002) 181-191.*
Majeti N.V. Ravi Kumar, Reactive & Functional Polymers 46 (2000) 1-27.*
Chen et al., J. Appl. Poly. Sci., 2001, 83(6), 1233-1241.*
Dutta et al., J. Sci. & Ind. Res., 2004, 63, 20-31.*
Collins English Dictionary (http://www.collinsdictionary.com/dictionary/english/gel).*
Laurati et al. ("Laurati", J. Chem. Phys, 2009, 130, 1-14.*
Domard, WO 97/03708 A1 (the '708) (translation from Espacenet (Aug. 21, 2015), 5 pages).*
Domard, WO 97/03708 A1, machine translation from Espacenet, French with corresponding English paragraphs (Aug. 21, 2015), 23 pages.*
Nimura, JP 10-1758587 A (the '587) (machine translation from AIPO, Aug. 21, 2015, 11 pages).*
International Search Report, Written Opinion and Article 34 Response filed from International Application No. PCT/US2008/053948 (Pub. No. WO 2008/103594).
International Search Report, Written Opinion and International Preliminary Report on Patentability from related International Application No. PCT/IB2007/000422 (Pub. No. WO 2007/096748).
Hawley's Condensed Chemical Dictionary, 14 Edition, pp. 538, 1053, Published by John Wiley & Sons, Inc., 2001.
Office Action, mailed Apr. 15, 2009, from related U.S. Appl. No. 11/677,319.
The Merck Manual of Diagnosis and Therapy, Seventeenth Edition, pp. 407-408, 459-460, Ed. Mark H. Beers, M.D. and Robert Berkow, M.D., published by Merck Research Laboratories, 1999.
Remington: The Science and Practice of Pharmacy, 20th Edition, pp. 281-288, Ed. Alfonso R. Gennaro, published by Lippincott Williams & Wilkins, 2000.
Silverman, R. B., The Organic Chemistry of Drug Design and Drug Action, pp. 4-47, published by Academic Press, 1992.
Sivakumar, M., et al., "Preparation, characterization and in-vitro release of gentamicin from coralline hydroxyapatite-chitosan composite microspheres," *Carbohydrate Polymers* 49:281-288, 2002.
"STN Database Descriptions," p. 52, 2006 Chemical abstracts catalog, published by Chemical Abstracts Service, 2006.

* cited by examiner

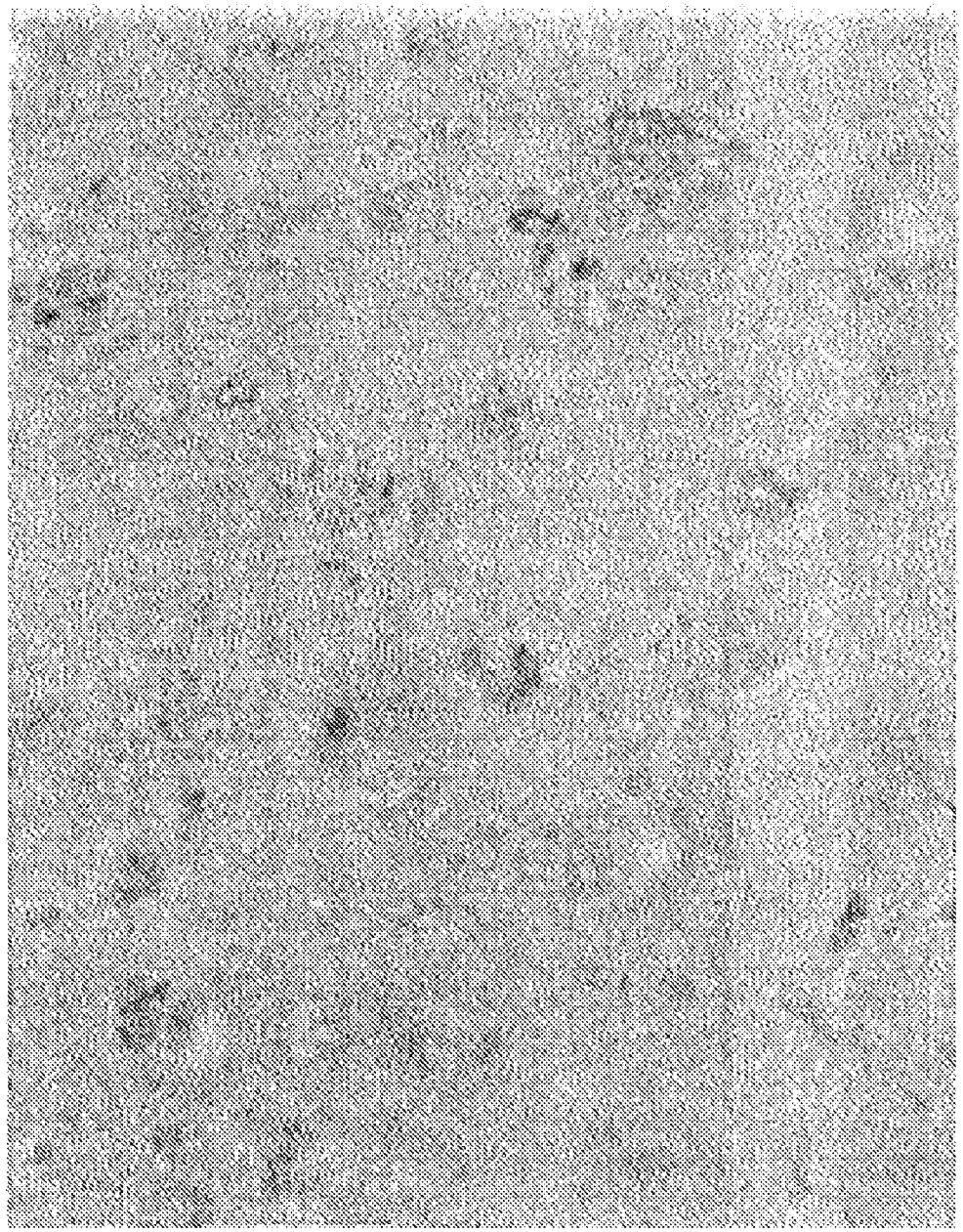

BIOMATERIAL, INJECTABLE IMPLANT COMPRISING IT, ITS METHOD OF PREPARATION AND ITS USES

The present invention claims priority to FR 06 01657, filed Feb. 24, 2006, the contents of which are hereby incorporated by reference.

FIELD OF INVENTION

The present invention relates to the field of biomaterials for implantation in the human or animal body. More particularly, the present invention relates to an implantable biomaterial, which may comprise chitin and/or chitosan. The biomaterial of this invention may be in the form of a gel, and may be injected, in particular by the subcutaneous or intradermal route, to form an implant. This implant has the benefit of being bioresorbable.

BACKGROUND OF INVENTION

Experts in the field are familiar with various injectable implants. For example, silicon gels (or silicon oils) are well-known, but these gels have the inconvenience of not being biodegradable. Moreover, silicon is often the cause of chronic inflammation, granuloma formation and even delayed allergic reactions. Collagen suspensions have also been very widely used over the past ten years. However, collagen generally is of bovine origin, which is undesirable for health and generally subject to additional regulatory requirements. Attempts to re-implant fatty cells removed from the patients themselves are also reported. However, the duration of the filling effect is generally less than the patient would like.

Other implants have been used, comprising a gelatine or collagen solution including, in suspension, polymethyl methacrylate (PMMA) microspheres having a diameter of 20 to 40 μm. PMMA, however, is not biodegradable and the gelatine or collagen solution is generally derived from bovine sources.

EP 0 969 883 describes an implantable gel including L-PLA (polylactic acid) microspheres with a diameter of 20 to 40 μm suspended in a carboxy methylcellulose gel (CMC). This gel is injectable and can be supplied in a sterile syringe. This product shows an acceptable efficacy but may present poor syringability (clogging of the required low-diameter needles may be noted) and a biodegradability which is too slow for some of the desired applications. The particles have the tendency to aggregate in the packaging, in particular in a syringe, making injections difficult and leading to inconsistent results. Non-homogeneous distribution of the particles in the injection area may actually be observed in patients. The expected aesthetic result is therefore not achieved and areas overloaded with particles are noted, sometimes adjacent to areas free of particles. The very long resorption time of the PLA (having a high molecular weight) may be of several years, which may also lead to inflammatory reactions in the long run.

There is therefore a real need for new biomaterials which do not have the drawbacks of the prior art, and particularly biomaterials which are useful as immediate filler materials, able to generate fibrosis and also capable of being resorbed to avoid chronic inflammatory reactions or rejection in the long run.

SUMMARY OF INVENTION

The inventors have found a biomaterial satisfying this need, which comprises an injectable composition, preferably in the form of a gel of chitin or chitosan, such as for example a succinochitosan glutamate gel, preferably including particles in suspension in the composition, said particles comprising chitin and/or chitosan. The biomaterial of the invention is bioresorbable, and when particles are in suspension they are bioresorbable, as well. The resorption time of the gel may be different from the resorption time of the particles.

According to the invention, the biomaterial of the invention produces a filling effect, resulting from the injected volume of composition. An important goal of the biomaterial of the invention is to induce fibrosis and tissue, especially neo-tissue (dermis), formation.

DESCRIPTION OF FIGURES

FIG. 1 is a photo showing the distribution of chitin particles for a succinochitosan glutamate gel containing 1% chitin particles. The photo of the biomaterial according to the invention, taken using an OLYMPUS® optical microscope, confirms that the particles are distributed homogeneously throughout the gel, naturally remaining in suspension due to the surfactant properties of chitosan, without the need of additional surfactants.

DETAILED DESCRIPTION OF THE INVENTION

Fibrosis is induced by biomaterial, which means by the composition and by the particles present in the biomaterial of the invention. When the biomaterial is injected, it is perceived as foreign bodies and the body responds to this attack by connective tissue hyperplasia, with proliferation of fibroblasts developing from collagen (neo-collagenesis). Fibrosis reaction induced by injecting the biomaterial of the invention may occur between 15 days and 3 weeks after injection.

Inducing fibrosis by injecting the biomaterial of the invention, is aimed to create natural filling tissue which will replace the biomaterial when it is resorbed. It is therefore desirable that the particles, which may be considered as being principally responsible for inducing the fibrosis, be resorbed once they no longer fulfill their function of inducing fibrosis, preferably within a period of 1 to 6 months.

Thus, the biomaterial according to the invention, partly because of the nature of its composition and partly because of the presence of particles, proposes a technical solution for patients in need for implantable filling material, and the product biodegradation and resorption time of the biomaterial may be adapted to the specific needs of the patients, for example by adjusting the amount of particles in the composition, thus avoiding the drawbacks of the prior art products.

Injecting a high amount of the biomaterial of the invention in a single injection may not be the optimal method of treating patients in need of said biomaterial, since the enhancement of the tissue (e.g., dermis) may not depend on the amount of biomaterial injected in a single injection ; it may be preferred to carry out several injections, which may be distant of a few weeks, for example two months. This embodiment aims at letting the biomaterial almost totally resorb before injecting new biomaterial.

In the present invention, by syringability is meant the ease of injection of the biomaterial; syringability generally may be a function of viscosity and other rheological properties of the biomaterial and of the size of the particles included within the biomaterial and of diameter of the needle of the syringe. By chitin, is meant a linear polysaccharide of beta-1.4-N-acetyl-D-glucosamine. By chitosan is meant a linear polysaccharide composed of randomly distributed linked beta-1.4-linked N-acetyl-D-glucosamine (acetylated unit) and D-glucosamine (deacetylated unit). The degree of deacetylation of chitosan may be determined by NMR spectroscopy.

By chitosan derivative, is meant any chitosan salt or acid-derived chitosan, chitosan glycolate, chitosan lactate, chitosan succinate, hydroxyalkyl chitosan, chitosan acetate, chitosan glutamate and more preferably succinochitosan glutamate.

According to a preferred embodiment of the invention, the biomaterial of the invention comprises or consists of an injectable bioresorbable polysaccharide composition, preferably in the form of a gel, including resorbable particles in suspension within the composition, said particles comprising chitin and/or chitosan.

In one embodiment, the polysaccharide is chitosan or a derivative thereof, preferably having a degree of deacetylation of about 30 to about 95%, preferably about 70 to about 90%, more preferably about 75 to about 85%, even more preferably about 80 to about 85%, and most preferably about 85%.

Advantageously, the molecular weight of the chitosan or the chitosan derivative of the gel composition or used to make the chitin or chitosan particles is of about 10 000 to about 500 000 D, preferably about 30 000 to about 100 000 D, more preferably about 50 000 to about 80 000 D.

According to an embodiment, the biomaterial includes in its composition about 0.1 to about 20%, preferably about 1 to about 20% w/w, more preferably about 1 to about 12% w/w, even more preferably about 1 to about 10%, most preferably about 1 to about 5% w/w of polysaccharide which is a chitosan or a chitosan derivative. In a specific embodiment, when the polysaccharide is a chitosan derivative, the composition of the biomaterial may include about 0.1 to about 20% of polysaccharide. According to a particularly preferred embodiment the chitosan derivative is succinochitosan glutamate.

According to an embodiment, the biomaterial of the invention comprises an injectable bioresorbable polysaccharide composition wherein the polysaccharide is succinochitosan glutamate. Advantageously, the succinochitosan glutamate has a degree of deacetylation of about 30 to about 95%, preferably about 70 to about 90%, more preferably about 75 to about 85%, even more preferably about 80 to about 85%, and most preferably about 85%. According to an embodiment, the succinochitosan glutamate has a molecular weight of about 10 000 to about 500 000 D, preferably about 30 000 to about 100 000 D, more preferably about 50 000 to about 80 000 D. According to an embodiment, the composition comprises about 0.1 to 20%, preferably 1 to 10%, more preferably 1 to 5% w/w succinochitosan glutamate by weight of the total composition. Advantageously, the biomaterial of the invention is a gel. The succinochitosan glutamate may be derived from chitosan of animal or vegetal origin. Advantageously, the succinochitosan glutamate used to manufacture the biomaterial of the invention is derived from GMP-grade chitosan.

In another preferred aspect of the invention, the biomaterial is a chitosan or chitosan derivative gel including chitin particles.

According to a most preferred embodiment of the invention, the biomaterial is a gel of succinochitosan glutamate, including chitin particles in suspension within the gel.

According to an embodiment, the chitosan used for manufacturing the biomaterial of the invention may be either of animal or vegetal origin. The use of a chitosan of animal origin, and more particularly crustaceans (prawn shells) or squids is of economic benefit. The use of a product of vegetal origin, and more particularly fungal, is generally better appreciated by consumers. Thus, according to a preferred embodiment, the chitosan used in the biomaterial of the invention, is extracted from fungi, such as for example Mucoralean strains, *Mucor racemosus* and *Cunninghamella elegans, Gongronella butleri, Aspergillus niger, Rhizopus oryzae, Lentinus edodes, Pleurotus sajo-caju*, more preferably *Agaricus bisporus*. According to another embodiment, the chitosan was produced from two yeasts, such as, for example *Zygosaccharomyces rouxii* and *Candida albicans*.

According to a particular embodiment of the invention, the particles included within the biomaterial of the invention contain or consist essentially of chitin and/or chitosan which are either of animal or vegetal origin. The particles may also be made of, or include, a mixture of chitin and chitosan. According to an embodiment, these particles may consist solely of chitin or solely of chitosan. According to an embodiment, the chitosan used to make the particles may have a degree of deacetylation of about 30 to about 95%, preferably about 70 to about 90%, more preferably about 75 to about 85%, even more preferably about 80 to about 85%, and most preferably about 85%. Advantageously, the chitosan used to make the particles of the invention may be of GMP grade. According to a preferred embodiment, the particles are of chitin obtained by reacetylation of a GMP grade chitosan. According to a preferred embodiment, the biomaterial of the invention is essentially free of endotoxins. According to another embodiment, the biomaterial includes deproteinized chitin particles essentially free of endotoxins.

According to an embodiment, the particles included within the biomaterial of the invention have a bioresorption time of 1 to 6 months. According to an embodiment, the chitin-only particles with a bioresorption time of 1 to 3 months, and chitosan-only particles have a bioresorption time of 1 to 4 months.

According to another embodiment of the invention, the amount of particles in the biomaterial of the invention may be of about 0.1 to about 10% w/w, preferably of 1 to 5% w/w, more preferably of 1 to 2% w/w.

The amount of particles included within the biomaterial of the invention may depend on the final application of the biomaterial and of the desired effect.

According to a preferred embodiment, the biomaterial of the invention is a chitosan or chitosan derivative gel, including 1 to 5% of chitosan particles or 1 to 5% of chitin particles. According to another embodiment, the biomaterial of the invention is a chitosan derivative gel, including 1 to 2% chitin particles. In a particularly preferred embodiment, the biomaterial of the invention is a gel consisting essentially of a chitosan derivative and water with chitin and/or chitosan particles suspended in the gel, where the gel is essentially free of any other formulation-enhancing agents such as plasticizers, surfactants, viscosity modifiers, and the like.

According to another embodiment of the invention, the particles included within the biomaterial of the invention have a mean diameter of about 3 to 150 µm, preferably 5 to 40 µm. According to an embodiment, the mean diameter of the particles are 3 to 12 µm, and preferably of 5 to 10 µm. According to another embodiment, the mean diameter of the particles are 10 to 32 µm. Preferably, the particles are microspheres.

Furthermore, these bioresorbable particles in suspension in the biomaterial of the invention should have a diameter such that the syringability of the product using 27 G (or possibly 30 G) needles remains satisfactory.

According to an embodiment, chitin and/or chitosan particles are obtained from chitin or chitosan crystals, having an average granulometry at the outset of 200 to 300 µm. The granulometry is reduced by any suitable technique known by one skilled in the art to lower the particle size of the particles, such as for example, but not limitatively, spray drying or micronization, optionally repeated more than once. These particles may then undergo a successive series of micronizations, while avoiding cryomicronization which sometimes damages the integrity of the micronized molecules. Subsequent sifting steps eliminate those particles which have a granulometry which is either too large or too small.

According to an embodiment, the particles of the invention do not contain polymethacrylic acid and/or ester derivative thereof containing hydroxyl group, polyacrylamide, polymethacrylamide, poly-N-vinyl-2-pyrrolidone, polyvinyl alcohol.

According to another embodiment, the particles are not composite, but made of a single ingredient, which is preferably chitin.

According to an advantageous embodiment, the biomaterial of the invention has a pH which is compatible with dermatological use, preferably a pH between 6.5 and 7.5, and ideally between 6.8 and 7.2.

According to another embodiment of the invention, the density of the biomaterial of the invention is comparable to that of the particles, preferably between 0.95 and 1.20, and ideally between 1.00 and 1.10.

The particles may be maintained in suspension by the viscosity of the particle-containing gel, the natural surfactant effect of chitin and chitosan, and also through the small size of the particles and the fact that their density is more or less equal to that of the gel. This homogeneity of density, the surfactant properties of chitin and chitosan and the small particle size ensures satisfactory homogeneity of the gel, avoiding clump formation which may block the fine needles, and avoiding the need for additional formulation-modifying agents such as plasticizers, surfactants, and viscosity modifiers.

The invention also details a process for manufacturing a biomaterial comprising an injectable bioresorbable polysaccharide composition containing resorbable chitin and/or chitosan particles in suspension, the said process involving steps in which chitosan or chitosan derivative with a degree of deacetylation of about 30 to about 95%, preferably about 70 to about 90%, more preferably about 75 to about 85%, even more preferably about 80 to about 85%, and most preferably about 85% is dissolved, followed by successive addition of glutamic acid and then succinic anhydrid, and neutralization. The addition of particles containing chitin and/or chitosan under agitation may be performed at various stages in the process, for example before or after addition of glutamic acid or at the end of the process.

During the neutralization step, the pH of this biomaterial is adjusted to somewhere between 6.5 and 7.5, ideally between 6.8 and 7.2, by addition of a base such as sodium hydroxide or triethanolamine.

The resulting biomaterial may not be affected by either pH or temperature. The latter is of particular interest as this means the product remains stable when stored at room temperature.

The process of manufacturing according to the invention preferably also includes a sterilization step, such as a step involving irradiation or steam sterilization for example.

According to an embodiment of the invention, the chitin and the chitosan used for manufacturing the biomaterial of the invention and/or the particles are from one source, which is preferably GMP-grade chitosan. According to another embodiment, the manufacturing process of the chitin particles suspended in the biomaterial uses chitin obtained by reacetylation of a GMP-grade chitosan. According to an embodiment of the invention, the chitin used in the manufacturing process of the composition and/or of the particles is essentially free of protein.

The invention also relates to a medical device containing the said biomaterial. According to a specific embodiment of the medical device, the said biomaterial is ready-to-use in a sterile syringe.

Another aspect of this invention relates to a method for aesthetic repair treatment, in which the said biomaterial is injected by a subcutaneous or intradermal route to fill a cavity of the face or body in either humans or animals. More specifically, a major application of the invention is facial restructuring for patients suffering from lipoatrophy, in particular those patients suffering from the HIV virus.

Lipoatrophy is characterized by a wasting of subcutaneous adipose tissue. In the face, wasting of the cheeks fat pads brings about this very characteristic morphological change. These fat pads are situated in the middle region of the cheek with various extensions in the facial region which can be affected by the fairly marked wasting of fatty tissue. In particular, the main loss may be seen in the sinus extension which gives a very sunken appearance to the face, although very often there is also characteristic sinking of the temporal region. This atrophy is also very often accompanied by a wasting of retro-orbital adipose tissue, resulting in enophthalmia which further exacerbates the facial deterioration. Lipoatrophy results in a very degrading unwell or morbid physical appearance in patients who, paradoxically, tend to have a satisfactory immune and virological status.

For this reason, patients oblivious to the efficacy of triple therapy may only consider the destructive effects on their physical appearance and may not think twice about jeopardizing their treatment, failing to take the treatment properly or at the very least taking it with a great deal of apprehension and despair.

Another object of the invention is the use of the said biomaterial as an injectable implant in aesthetic treatment, to fill wrinkles, fine lines, skin depressions, acne scars and other scars.

Another subject of the invention is a method of aesthetic treatment to fill a cavity in the human face or body, which may involve several successive injections of the said biomaterial, particularly in the case of lipoatrophy, whereby each injection could be followed by massage of the surface of the skin over the injection area.

Another subject of the invention is the use of the said biomaterial to fill gingiva cavities or as a gingival filler.

Another subject of the invention is the use of the said biomaterial in manufacturing a medical device aimed to be implanted in persons suffering from stress urinary incontinence alone or in association with other forms of continence. The said biomaterial is therefore used to fill a deficient urethral sphincter which occurs in 10 to 15% of active women suffering from a urinary incontinence syndrome. In the present absence of any satisfactory treatment, this particle gel would fulfill a special role as a very non-invasive treatment compared with the surgical procedures currently available. This method is non-aggressive, reproducible, without side-effects and only involves a local anaesthetic followed by the para-urethral injection of the particle gel through the vaginal wall or above the urethra between the urethra and the pubic bone (an injection of around 1 to 4 cc).

The invention will be better understood upon reading the example detailed below, which illustrates in a non-limiting manner particular embodiments of the invention:

EXAMPLE 1

Gel Containing 4% of CHITOSAN (w/w)

Chitosan, GMP crustacean source, degree of deacetylation 85%, intrinsic viscosity of approx 150 cps (in a 1% acetic acid solution) was dissolved in purified water. Glutamic acid was added in stoicchiometric quantity (according to DDA) in the solution, which, after 15 to 20 minutes, produced chitosan glutamate. Succinic anhydride was then added (same quantity as glutamic acid) yielding a gel in the form of succino-chitosan glutamate. The pH of the gel was adjusted to 6,8-7,2 with sodium hydroxide. Gel was then filtered through a 160 μm filter to eliminate any possible undesired particle. Purified water was then added so as to obtain a 4% concentration of pure Chitosan in the gel. Gel obtained had a viscosity of approx 2500 cps, and was easy to inject through a 30 gauge needle. It was not sensitive to pH or temperature.

EXAMPLE 2

Gel Containing 2% of CHITOSAN, in which 1% CHITIN Microspheres (w/w) were in Suspension.

A gel was prepared in the same way as in example 1, except for the concentration which was adjusted to 2% of pure CHITOSAN (w/w). Simultaneously, Chitosan was dissolved in a 1% acetic acid solution, and ethanol was added in a proportion of 30% of the final solution. A Büchi type spray-dryer was then used in order to obtain Chitosan microspheres, with a granulometry of 5 to 13 μm. These microspheres were poured into an acetic solution (stoicchiometric quantity of acetic acid calculated on DDA, so as to be able to reacetylate 25 to 30% of the polymer, so as to obtain more than 50% final acetylation). The resulting chitin microspheres were then incorporated into the gel so as to have 1% microspheres (w/w). The final colloidal suspension had a viscosity of approx 3500 cps, which made it easy to inject through a 27 gauge needle, and was not sensitive to pH or temperature.

EXAMPLE 3

Gel Containing 5% of CHITOSAN, in which 1% CHITIN Micronized Particles (w/w) were in Suspension.

A gel was prepared in the same way as in example 1, except for the concentration which was adjusted to 5% of pure CHITOSAN (w/w). Genuine CHITIN was obtained from the GMP Chitosan supplier. The granulometry of this powder was 200-300 μm. The powder was micronized and sieved so as to obtain a powder with a granulometry of 5 to 32 μm. Chitin particles were then incorporated into the gel so as to have 1% suspension in the gel. The final suspension had a viscosity of approx 4500 cps, and it was still possible to inject it through a 27 gauge needle. The final product was not sensitive to pH or temperature.

What is claimed is:

1. An injectable gel comprising (a) a gel portion and (b) solid resorbable powder particles in suspension in the gel portion;
    (i) wherein the solid resorbable powder particles consist essentially of chitin powder;
    (ii) wherein the injectable gel comprises from 0.1 wt. % to 10 wt. % of the solid resorbable powder particles by total weight of the injectable gel;
    (iii) wherein the gel portion comprises from 0.1 wt. % to 20 wt. % of a succinylated chitosan by total weight of the injectable gel;
    (iv) wherein the injectable gel has a viscosity that is suited for subcutaneous or intradermal injection into a human.
2. The injectable gel according to claim 1, wherein the solid resorbable powder particles have a bioresorption time of 1 to 6 months.
3. A medical device containing the injectable gel of claim 1.
4. A medical device according to claim 3, in which the injectable gel is ready-to-use in a sterile syringe.
5. The injectable gel according to claim 1, wherein the solid resorbable powder particles have a mean diameter of about 3 to about 150 μm.
6. The injectable gel of claim 1, wherein the injectable gel has a pH of from 6.5 to 7.5.
7. The injectable gel of claim 1, wherein the injectable gel has a pH of from 6.8 to 7.2.
8. The injectable gel of claim 1, wherein the succinylated chitosan is succinochitosan glutamate.

* * * * *